United States Patent
Yokota

(10) Patent No.: US 11,884,583 B2
(45) Date of Patent: Jan. 30, 2024

(54) METHOD FOR PRODUCING COLORED GLASS FOR PHARMACEUTICAL CONTAINERS AND COLORED GLASS FOR PHARMACEUTICAL CONTAINERS

(71) Applicant: Nippon Electric Glass Co., Ltd., Shiga (JP)

(72) Inventor: Yuki Yokota, Shiga (JP)

(73) Assignee: NIPPON ELECTRIC GLASS CO., LTD., Shiga (JP)

( * ) Notice: Subject to any disclaimer, the term of this patent is extended or adjusted under 35 U.S.C. 154(b) by 1011 days.

(21) Appl. No.: 16/619,139

(22) PCT Filed: Jun. 4, 2018

(86) PCT No.: PCT/JP2018/021392
§ 371 (c)(1),
(2) Date: Dec. 4, 2019

(87) PCT Pub. No.: WO2018/225691
PCT Pub. Date: Dec. 13, 2018

(65) Prior Publication Data
US 2020/0140312 A1   May 7, 2020

(30) Foreign Application Priority Data

Jun. 6, 2017 (JP) .................. 2017-111478

(51) Int. Cl.
| | | |
|---|---|---|
| *C03C 3/091* | (2006.01) | |
| *A61M 5/178* | (2006.01) | |
| *C03B 1/00* | (2006.01) | |
| *C03C 4/02* | (2006.01) | |

(52) U.S. Cl.
CPC ............. *C03C 3/091* (2013.01); *A61M 5/178* (2013.01); *C03B 1/00* (2013.01); *C03C 4/02* (2013.01); *C03C 2203/10* (2013.01)

(58) Field of Classification Search
CPC ......... C03C 3/085; C03C 3/087; C03C 3/091; C03C 4/02; C03C 4/20; C03C 4/085
See application file for complete search history.

(56) References Cited

U.S. PATENT DOCUMENTS

| | | | |
|---|---|---|---|
| 2005/0061033 A1* | 3/2005 | Petrany | C03C 3/093 501/67 |
| 2020/0283331 A1 | 9/2020 | Arai | |

FOREIGN PATENT DOCUMENTS

| | | |
|---|---|---|
| JP | 47-5269 | 2/1972 |
| JP | 01-286936 | 11/1989 |
| JP | 2608535 | 2/1997 |
| JP | 2005-170735 | 6/2005 |
| JP | 2014-24731 | 2/2014 |
| JP | 2015-193521 | 11/2015 |
| WO | 2019/078188 | 4/2019 |

OTHER PUBLICATIONS

Extended European Search Report dated Jan. 22, 2021, in corresponding European Patent Application No. 18813787.1.
International Search Report (ISR) dated Aug. 7, 2018 in International (PCT) Application No. PCT/JP2018/021392.
International Preliminary Report on Patentability dated Dec. 10, 2019 in corresponding International (PCT) Patent Application No. PCT/JP2018/021392.

* cited by examiner

*Primary Examiner* — Elizabeth A. Bolden
(74) *Attorney, Agent, or Firm* — Wenderoth, Lind & Ponack, L.L.P.

(57) ABSTRACT

The present invention relates to a method of producing a colored glass for a pharmaceutical container by which the transmittance of a glass to be obtained is easily controlled so as to satisfy the standards of the Japanese Pharmacopoeia.

2 Claims, No Drawings

METHOD FOR PRODUCING COLORED GLASS FOR PHARMACEUTICAL CONTAINERS AND COLORED GLASS FOR PHARMACEUTICAL CONTAINERS

TECHNICAL FIELD

The present invention relates to a method of producing a colored glass for a pharmaceutical container and a colored glass for a pharmaceutical container.

BACKGROUND ART

Pharmaceutical containers typified by a syringe and a cartridge have two kinds of color tones, colorless and colored. Out of such pharmaceutical containers, a colored container is required to have a function of blocking ultraviolet light so that a pharmaceutical included therein is not altered through light irradiation.

Incidentally, with regard to the light shading property of a pharmaceutical colored container, in each of the European Pharmacopoeia and the United States Pharmacopeia, it is specified that a light transmittance measured at wavelength intervals of 20 nm is 50% or less in a short-wavelength region (from 290 nm to 450 nm).

Meanwhile, in the Japanese Pharmacopoeia, Sixteenth Edition, section 7.01 (hereinafter referred to as the Japanese Pharmacopoeia), with regard to the light shading property of a pharmaceutical colored container, in addition to the above-mentioned standard of a transmittance in a short-wavelength region (from 290 nm to 450 nm), there are two kinds of standards of a transmittance in a long-wavelength region (from 590 nm to 610 nm) depending on a thickness. Specifically, it is specified that the transmittance in a long-wavelength region (from 590 nm to 610 nm) is 60% or more in the case of a container having a thickness of less than 1 mm and is 45% or more in the case of a container having a thickness of 1 mm or more. Accordingly, in order to obtain a pharmaceutical colored container which satisfies the standards of the Japanese Pharmacopoeia, it is required in a colored glass for a pharmaceutical container that the transmittance of the glass be strictly controlled depending on the thickness of the glass to be formed.

In this connection, the colored glass for a pharmaceutical container is produced by melting a glass batch including a coloring component to obtain a glass melt, and then forming the glass melt into a desired shape, followed by cooling.

For example, in Patent Literature 1, there is described an amber-colored borosilicate glass including $Fe_2O_3$ and $TiO_2$ as coloring components in a glass composition. In Patent Literature 1, a transmittance is controlled by adjusting the contents of $Fe_2O_3$ and $TiO_2$.

CITATION LIST

Patent Literature 1: JP 2608535 B2

SUMMARY OF INVENTION

Technical Problem

However, it is difficult to finely control the transmittance of the glass merely by changing the contents of the coloring components in the glass composition. Besides, in the Japanese Pharmacopoeia, there are two kinds of standards of a transmittance in a long-wavelength region (from 590 nm to 610 nm) depending on a thickness, and hence, for example, when the thickness of a product is significantly changed, for example, from 0.5 mm to 2 mm or more in the course of production, it is further difficult to control the transmittance of the glass.

The present invention has been made in view of the above-mentioned circumstances, and relates to a method of producing a colored glass for a pharmaceutical container by which the transmittance of a glass to be obtained is easily controlled so as to satisfy the standards of the Japanese Pharmacopoeia.

Solution to Problem

In order to solve the above-mentioned problems, the inventor of the present invention has made extensive investigations on the coloring mechanism of a colored glass for a pharmaceutical container. As a result, the inventor has found that the transmittance of the glass is not determined unambiguously by the contents of $Fe_2O_3$ and $TiO_2$, and relates to a redox state at the time of melting of the glass, and when a reducing agent is used, a product of the content of $Fe_2O_3$ and the content of $TiO_2$ in a glass composition closely relates to the transmittance of the colored glass for a pharmaceutical container. Moreover, the inventor has found that the above-mentioned problems can be solved by setting a value for the product of the content of $Fe_2O_3$ and the content of $TiO_2$ to fall within a certain range.

That is, according to one embodiment of the present invention, there is provided a method of producing a colored glass for a pharmaceutical container, comprising the steps of: blending a glass batch; melting the glass batch to obtain a glass melt; and forming the glass melt to obtain a formed glass, the step of blending a glass batch being performed by adding a reducing agent to the glass batch so that a glass comprising as a glass composition, in terms of mass %, 65% to 75% of $SiO_2$, 0% to 20% of $B_2O_3$, 1% to 10% of $Al_2O_3$, 1% to 10% of $R_2O$, where R represents at least one or more kinds of Li, Na, and K, 1% to 5% of R'O, where R' represents at least one or more kinds of Ca and Ba, 0.01% to 5% of $Fe_2O_3$, and 0.01% to 5% of $TiO_2$ and further satisfying a relational expression of $1.00 \leq [Fe_2O_3 \text{ (content of } Fe_2O_3)] \times [TiO_2 \text{ (content of } TiO_2)] < 6.00$ is obtained.

Herein, as described above, the transmittance of the glass relates to the redox state of the glass, and in general, the redox state of the glass closely relates to a melting temperature. Therefore, when a glass having a suitable transmittance is to be obtained, an approach to changing a melting temperature is conceivable. However, when production conditions, such as a melting temperature, are changed, the viscosity of the glass is also changed, resulting in a risk of a reduction in productivity. For example, when the melting temperature is excessively increased, the viscosity of the glass at the time of forming is excessively reduced, and it becomes difficult to obtain a desired shape.

In the one embodiment of the present invention, the reducing agent is used, and the product of the content of $Fe_2O_3$ and the content of $TiO_2$ in terms of mass % in the glass composition is strictly restricted as described above. With this, a colored glass for a pharmaceutical container in which a transmittance is easily controlled so as to satisfy the standards of the Japanese Pharmacopoeia can be obtained without reducing the productivity.

The "content of $Fe_2O_3$" as used herein refers to a value obtained by converting Fe having any valence in the glass into $Fe_2O_3$.

In the method of producing a colored glass for a pharmaceutical container according to the one embodiment of the present invention, it is preferred that a content of the reducing agent in the glass batch be from 0.01 mass % to 0.20 mass %.

Conceivable means for changing the redox state of the glass is to change the kind and content of the reducing agent, as well as to change the melting temperature as described above. However, the kind and content of the reducing agent also affect the fining property of the glass. Therefore, in order to maintain the productivity while an appropriate redox state and an appropriate fining effect are achieved, it is particularly desired that the content of the reducing agent be not significantly changed.

In the one embodiment of the present invention, the product of the content of $Fe_2O_3$ and the content of $TiO_2$ in terms of mass % in the glass composition is strictly restricted as described above, and hence the content of the reducing agent in the glass batch can be set to fall within the range of from 0.01 mass % to 0.20 mass %, and the productivity is less liable to be reduced. In addition, when the content of the reducing agent falls within the above-mentioned range, it is easy to obtain a colored glass for a pharmaceutical container which satisfies the standards of a transmittance of the Japanese Pharmacopoeia.

In the method of producing a colored glass for a pharmaceutical container according to the one embodiment of the present invention, it is preferred that the reducing agent comprise at least one kind of metal aluminum, metal sulfur, or carbon.

In the method of producing a colored glass for a pharmaceutical container according to the one embodiment of the present invention, it is preferred that a content of the metal aluminum in the glass batch be from 0.03 mass % to 0.13 mass %. In the one embodiment of the present invention, the product of the content of $Fe_2O_3$ and the content of $TiO_2$ is strictly restricted, and hence when the content of the metal aluminum falls within the above-mentioned range, it is easy to achieve a transmittance which satisfies the standards of the Japanese Pharmacopoeia. When the content of the metal aluminum is restricted to fall within the above-mentioned range, an influence on the fining property can be suppressed, and risks of a reduction in productivity and deterioration in glass quality are reduced.

Further, in the method of producing a colored glass for a pharmaceutical container according to the one embodiment of the present invention, it is preferred that the formed glass to be obtained have a thickness of less than 1 mm, and the blending a glass batch be performed so that a glass satisfying a relational expression of $1.20 \leq [Fe_2O_3 \text{ (content of } Fe_2O_3\text{)}] \times [TiO_2 \text{ (content of } TiO_2\text{)}]$ in terms of mass % is obtained.

As described above, in the Japanese Pharmacopoeia, there are two kinds of standards depending on the thickness of a pharmaceutical colored container. When the target thickness of the pharmaceutical colored container is less than 1 mm, the product of the content of $Fe_2O_3$ and the content of $TiO_2$ is further strictly restricted. With this, a colored glass for a pharmaceutical container in which a transmittance is easily controlled so as to satisfy the standards of the Japanese Pharmacopoeia in the case where the formed glass has a thickness of less than 1 mm, that is, a transmittance of 50% or less in a short-wavelength region (from 290 nm to 450 nm) and a transmittance of 60% or more in a long-wavelength region (from 590 nm to 610 nm) can be obtained.

Further, in the method of producing a colored glass for a pharmaceutical container according to the one embodiment of the present invention, it is preferred that the formed glass to be obtained have a thickness of 1 mm or more, and the blending a glass batch be performed so that a glass satisfying a relational expression of $[Fe_2O_3 \text{ (content of } Fe_2O_3\text{)}] \times [TiO_2 \text{ (content of } TiO_2\text{)}] \leq 5.95$ in terms of mass % is obtained.

When the target thickness of the pharmaceutical colored container is 1 mm or more, the product of the content of $Fe_2O_3$ and the content of $TiO_2$ is further strictly restricted. With this, a colored glass for a pharmaceutical container in which a transmittance is easily controlled so as to satisfy the standards of the Japanese Pharmacopoeia in the case where the formed glass has a thickness of 1 mm or more, that is, a transmittance of 50% or less in a short-wavelength region (from 290 nm to 450 nm) and a transmittance of 45% or more in a long-wavelength region (from 590 nm to 610 nm) can be obtained.

In addition, in the method of producing a colored glass for a pharmaceutical container according to the one embodiment of the present invention, it is preferred that the colored glass for a pharmaceutical container to be obtained satisfy a transmittance specified in "Light transmission test for light-resistant containers" of the Japanese Pharmacopoeia, section 7.01.

In addition, according to one embodiment of the present invention, there is provided a method of producing a colored glass for a container, comprising the steps of: blending a glass batch; melting the glass batch to obtain a glass melt; and forming the glass melt to obtain a formed glass, the step of blending a glass batch being performed by adding a reducing agent to the glass batch so that a glass comprising as a glass composition, in terms of mass %, 65% to 75% of $SiO_2$, 0% to 20% of $B_2O_3$, 1% to 10% of $Al_2O_3$, 1% to 10% of $R_2O$, where R represents at least one or more kinds of Li, Na, and K, 1% to 5% of R'O, where R' represents at least one or more kinds of Ca and Ba, 0.01% to 5% of $Fe_2O_3$, and 0.01% to 5% of $TiO_2$ and further satisfying a relational expression of $1.00 \leq [Fe_2O_3 \text{ (content of } Fe_2O_3\text{)}] \times [TiO_2 \text{ (content of } TiO_2\text{)}] < 6.00$ is obtained.

Further, according to one embodiment of the present invention, there is provided a colored glass for a pharmaceutical container, comprising as a glass composition, in terms of mass %, 65% to 75% of $SiO_2$, 0% to 20% of $B_2O_3$, 1% to 10% of $Al_2O_3$, 1% to 10% of $R_2O$, where R represents at least one or more kinds of Li, Na, and K, 1% to 5% of R'O, where R' represents at least one or more kinds of Ca and Ba, 0.01% to 5% of $Fe_2O_3$, and 0.01% to 5% of $TiO_2$, further satisfying a relational expression of $1.00 \leq [Fe_2O_3 \text{ (content of } Fe_2O_3\text{)}] \times [TiO_2 \text{ (content of } TiO_2\text{)}] < 6.00$, and satisfying a transmittance specified in "Light transmission test for light-resistant containers" of the Japanese Pharmacopoeia, section 7.01.

In addition, in the colored glass for a pharmaceutical container according to the one embodiment of the present invention, it is preferred that the colored glass have a thickness of less than 1 mm and satisfy a relational expression of $1.20 \leq [Fe_2O_3 \text{ (content of } Fe_2O_3\text{)}] \times [TiO_2 \text{ (content of } TiO_2\text{)}]$ in terms of mass %. With this, the transmittance of the colored glass for a pharmaceutical container according to the one embodiment of the present invention particularly easily satisfies the standards of the Japanese Pharmacopoeia.

In addition, in the colored glass for a pharmaceutical container according to the one embodiment of the present invention, it is preferred that the colored glass have a thickness of 1 mm or more and satisfy a relational expression of $[Fe_2O_3 \text{ (content of } Fe_2O_3\text{)}] \times [TiO_2 \text{ (content of } TiO_2\text{)}] \leq 5.95$ in terms of mass %. With this, the transmittance of the colored glass for a pharmaceutical container according to the one embodiment of the present invention particularly easily satisfies the standards of the Japanese Pharmacopoeia.

In addition, according to one embodiment of the present invention, there is provided a colored glass for a container, comprising as a glass composition, in terms of mass %, 65% to 75% of $SiO_2$, 0% to 20% of $B_2O_3$, 1% to 10% of $Al_2O_3$, 1% to 10% of $R_2O$, where R represents at least one or more kinds of Li, Na, and K, 1% to 5% of R'O, where R' represents at least one or more kinds of Ca and Ba, 0.01% to 5% of $Fe_2O_3$, and 0.01% to 5% of $TiO_2$ and further satisfying a relational expression of $1.00 \leq [Fe_2O_3 \text{ (content of } Fe_2O_3)] \times [TiO_2 \text{ (content of } TiO_2)] < 6.00$.

DESCRIPTION OF EMBODIMENTS

A method of producing a colored glass for a pharmaceutical container of the present invention is described below.

The method of producing a colored glass for a pharmaceutical container of the present invention comprises the steps of: blending a glass batch; melting the glass batch to obtain a glass melt; and forming the glass melt.

First, glass raw materials are weighed and mixed to blend a glass batch. The glass batch comprises a reducing agent and is blended so that a glass comprising as a glass composition, in terms of mass %, 65% to 75% of $SiO_2$, 0% to 20% of $B_2O_3$, 1% to 10% of $Al_2O_3$, 1% to 10% of $R_2O$, where R represents at least one or more kinds of Li, Na, and K, 1% to 5% of R'O, where R' represents at least one or more kinds of Ca and Ba, 0.01% to 5% of $Fe_2O_3$, and 0.01% to 5% of $TiO_2$ and further having a product of the content of $Fe_2O_3$ and the content of $TiO_2$ satisfying a relational expression of $1.00 \leq [Fe_2O_3 \text{ (content of } Fe_2O_3)] \times [TiO_2 \text{ (content of } TiO_2)] < 6.00$ is obtained. Natural raw materials and chemical raw materials may be used for the glass batch, and as well, a glass cullet may also be used for the glass batch as required.

Next, the blended glass batch is loaded into a melting furnace and melted to obtain a glass melt. From the viewpoint of a fining property, the melting temperature of the glass is preferably from 1,350° C. to 1,700° C., more preferably from 1,500° C. to 1,700° C. or from 1,550° C. to 1,700° C., particularly preferably from 1,600° C. to 1,700° C.

Subsequently, the glass melt obtained as described above is formed into a desired shape, such as a tubular shape or a sheet shape, followed by annealing to obtain a formed glass. A glass forming method is not limited, and any method suitable for obtaining a desired shape may be appropriately adopted. For example, when the glass melt is formed into a tubular shape, the Danner method, a blow method, a down-draw method, an up-draw method, or the like may be adopted. In addition, as required, the obtained formed glass may be subjected to end surface treatment or fusing treatment.

As described above, the transmittance of the glass is not determined by the contents of $Fe_2O_3$ and $TiO_2$ alone, and relates to the redox state of the glass. However, in the present invention, the product of the content of $Fe_2O_3$ and the content of $TiO_2$ is strictly restricted, and hence a colored glass for a pharmaceutical container in which the transmittance of the glass is easily controlled so as to satisfy the standards of the Japanese Pharmacopoeia can be obtained without significantly changing production conditions, such as a melting temperature, and the content of the reducing agent.

The product of the content of $Fe_2O_3$ and the content of $TiO_2$ in terms of mass % is set as follows: a relational expression of $1.00 \leq [Fe_2O_3 \text{ (content of } Fe_2O_3)] \times [TiO_2 \text{ (content of } TiO_2)] < 6.00$ is satisfied, and the product is preferably 1.20 or more, 1.40 or more, 1.60 or more, 1.80 or more, or 1.90 or more. In addition, the product of the content of $Fe_2O_3$ and the content of $TiO_2$ in terms of mass % is preferably 5.95 or less, 5.50 or less, 5.00 or less, 4.50 or less, 4.00 or less, 3.50 or less, 3.30 or less, 3.00 or less, or 2.90 or less, particularly preferably 2.80 or less. With this, while productivity is maintained, a colored glass for a pharmaceutical container in which the transmittance of the glass is easily controlled so as to satisfy the standards of the Japanese Pharmacopoeia can be obtained. Meanwhile, when the product of the content of $Fe_2O_3$ and the content of $TiO_2$ is outside the above-mentioned range, a value for the transmittance of an actual product and a value for the transmittance specified in the Japanese Pharmacopoeia are excessively apart from each other, and it becomes difficult to control the transmittance so as to satisfy the standards of the Japanese Pharmacopoeia. In order to obtain a product which satisfies the standards of the Japanese Pharmacopoeia, it is required that the production conditions, such as a melting temperature, and the content of the reducing agent be significantly changed, resulting in high risks of a reduction in productivity and deterioration in glass quality.

In the present invention, the glass batch further comprises the reducing agent. A sulfide, metal sulfur, metal aluminum, chromite, carbon, coke, silicon, or the like may be used as the reducing agent.

The content of the reducing agent in the glass batch in terms of mass % is preferably from 0.01% to 0.20%, from 0.02% to 0.18%, from 0.03% to 0.15%, from 0.03% to 0.13%, or from 0.04% to 0.12%, particularly preferably from 0.06% to 0.10%. The content of the reducing agent not only contributes to the redox state, but also affects the fining property of the glass. Therefore, when the content of the reducing agent is too large, an optimum fining effect cannot be obtained, and when the content of the reducing agent is too small, the redox state is difficult to control, and further the fining effect becomes poor. When the content of the reducing agent is outside the above-mentioned range, a reduction in productivity and deterioration in glass quality occur.

When metal aluminum is used as the reducing agent, the content thereof in terms of mass % is preferably from 0.03% to 0.13%, from 0.04% to 0.12%, or from 0.05% to 0.10%, particularly preferably from 0.06% to 0.09%. The use of metal aluminum as the reducing agent is preferred because, when an aluminum component is included in the glass composition, metal aluminum is incorporated in the glass composition, and hence an inconvenience, such as elution, is less liable to occur at the time when the glass is turned into a pharmaceutical container.

In addition, in the present invention, the product of the content of $Fe_2O_3$ and the content of $TiO_2$ is further strictly restricted in accordance with the target thickness of the formed glass. With this, the transmittance specified in the Japanese Pharmacopoeia is further easily satisfied.

Specifically, when a formed glass having a thickness of less than 1 mm is to be obtained, the product of the content of $Fe_2O_3$ and the content of $TiO_2$ is set as follows: a relational expression of $1.20 \leq [Fe_2O_3 \text{ (content of } Fe_2O_3)] \times [TiO_2 \text{ (content of } TiO_2)]$ is preferably satisfied, and the product is preferably 1.40 or more, 1.60 or more, 1.80 or more, 2.00 or more, 2.20 or more, 2.40 or more, or 2.60 or more, particularly preferably 2.80 or more. With this, in the case of having a thickness of less than 1 mm, a colored glass for a pharmaceutical container in which a transmittance is easily controlled so as to satisfy the standards of the Japanese Pharmacopoeia can be obtained without reducing the productivity. While the transmittance of the formed glass varies depending on the thickness, when a value for the product is too small, the degree of coloration of the glass is reduced, and hence, out of the standards of the Japanese Pharmacopoeia in the case of a container having a thickness of less than 1 mm, the standard of a transmittance of 50% or less in a short-wavelength region (from 290 nm to 450 nm) is difficult to satisfy.

In addition, as a form of the formed glass having a thickness of less than 1 mm, for example, various thicknesses, such as 0.9 mm or less, 0.7 mm or less, 0.6 mm or less, 0.4 mm or less, 0.3 mm or less, and 0.2 mm or less, may each be selected.

In addition, when the thickness of the formed glass is less than 1 mm, the content of metal aluminum in the glass batch in terms of mass % is preferably from 0.06% to 0.13%, from 0.07% to 0.12%, from 0.08% to 0.11%, or from 0.09% to 0.11%. With this, the transmittance of the colored glass for a pharmaceutical container can satisfy the standards of the Japanese Pharmacopoeia without a reduction in productivity and deterioration in glass quality.

As another form, when a formed glass having a thickness of 1 mm or more is to be obtained, the product of the content of $Fe_2O_3$ and the content of $TiO_2$ is set as follows: a relational expression of [$Fe_2O_3$ (content of $Fe_2O_3$)]×[$TiO_2$ (content of $TiO_2$)]≤5.95 is preferably satisfied, and the product is preferably 5.40 or less, 4.90 or less, 4.40 or less, 3.90 or less, 3.50 or less, 3.20 or less, 3.10 or less, 2.90 or less, 2.70 or less, 2.50 or less, 2.30 or less, 2.10 or less, or 1.90 or less, particularly preferably 1.85 or less. With this, in the case of having a thickness of 1 mm or more, a colored glass for a pharmaceutical container in which a transmittance is easily controlled so as to satisfy the transmittance specified in the Japanese Pharmacopoeia can be obtained without reducing the productivity. While the transmittance of the formed glass varies depending on the thickness, when a value for the product is too large, the degree of coloration of the glass is excessively increased, and hence, out of the standards of the Japanese Pharmacopoeia in the case of a container having a thickness of 1 mm or more, the standard of a transmittance of 45% or more in a long-wavelength region (from 590 nm to 610 nm) is difficult to satisfy.

As a form of the formed glass having a thickness of 1 mm or more, for example, various thicknesses, such as 1.3 mm or more, 1.5 mm or more, 1.9 mm or more, 2.0 mm or more, 2.3 mm or more, and 2.6 mm or more, may each be selected.

In addition, when the thickness of the formed glass is 1 mm or more, the content of metal aluminum in the glass batch in terms of mass % is preferably from 0.03% to 0.10%, from 0.04% to 0.09%, or from 0.05% to 0.08%, particularly preferably from 0.05% to 0.07%. With this, the transmittance of the colored glass for a pharmaceutical container can satisfy the standards of the Japanese Pharmacopoeia without a reduction in productivity and deterioration in glass quality.

In addition, the ratio between the content of $Fe_2O_3$ and the content of $TiO_2$ is set as follows: a relational expression of 0.10≤[$Fe_2O_3$ (content of $Fe_2O_3$)]/[$TiO_2$ (content of $TiO_2$)] ≤0.50 is preferably satisfied, and the ratio is preferably 0.10 or more, 0.15 or more, 0.20 or more, 0.45 or less, or 0.40 or less, particularly preferably 0.30 or less. With this, coloration in reddish-brown by virtue of an Fe—O—Ti structure is easily expressed, and the transmittance of the glass is easily controlled so as to satisfy the transmittance specified in the Japanese Pharmacopoeia in a wide range of thicknesses.

A raw material to be used as an iron raw material is not particularly limited, and it is preferred to use at least one or more kinds of ferrous oxide, ferric oxide, and triiron tetraoxide. The iron raw material may be selected in accordance with the target redox state of the glass melt. Specifically, it is appropriate to use ferrous oxide when serving on a reduction side is required, and to use ferric oxide when serving on an oxidation side is required.

In the method of producing a colored glass for a pharmaceutical container of the present invention, it is preferred that the colored glass for a pharmaceutical container to be obtained satisfy a transmittance specified in "Light transmission test for light-resistant containers" of the Japanese Pharmacopoeia, section 7.01.

In addition, while the above-mentioned production method is suitable as a method of producing a colored glass for a pharmaceutical container, its applications are not limited to pharmaceutical container applications, and the above-mentioned production method may also be used as a method of producing a colored glass for a container other than the pharmaceutical container.

The content of the reducing agent in the glass batch and the kind of the reducing agent, the contents of $Fe_2O_3$ and $TiO_2$ and the relational expression established therebetween, and other preferred ranges are the same as in the above-mentioned method of producing a colored glass for a pharmaceutical container, and hence the description thereof is omitted herein.

A colored glass for a pharmaceutical container of the present invention can be easily obtained by the above-mentioned method of producing a colored glass for a pharmaceutical container.

That is, the colored glass for a pharmaceutical container of the present invention comprises as a glass composition, in terms of mass %, 65% to 75% of $SiO_2$, 0% to 20% of $B_2O_3$, 1% to 10% of $Al_2O_3$, 1% to 10% of $R_2O$, where R represents at least one or more kinds of Li, Na, and K, 1% to 5% of R'O, where R' represents at least one or more kinds of Ca and Ba, 0.01% to 5% of $Fe_2O_3$, and 0.01% to 5% of $TiO_2$, further satisfies a relational expression of 1.00≤[$Fe_2O_3$ (content of $Fe_2O_3$)]×[$TiO_2$ (content of $TiO_2$)]<6.00, and satisfies a transmittance specified in "Light transmission test for light-resistant containers" of the Japanese Pharmacopoeia, section 7.01.

In addition, in the colored glass for a pharmaceutical container of the present invention, it is preferred that the colored glass have a thickness of less than 1 mm and satisfy a relational expression of 1.20≤[$Fe_2O_3$ (content of $Fe_2O_3$)]× [$TiO_2$ (content of $TiO_2$)] in terms of mass %.

Further, in the colored glass for a pharmaceutical container of the present invention, it is preferred that the colroed glass have a thickness of 1 mm or more and satisfy a relational expression of [$Fe_2O_3$ (content of $Fe_2O_3$)]×[$TiO_2$ (content of $TiO_2$)]≤5.95 in terms of mass %.

When a value for the product of the content of $Fe_2O_3$ and the content of $TiO_2$ is further strictly restricted as described above, the transmittance of the glass to be obtained can easily satisfy the standards of the Japanese Pharmacopoeia.

The reasons why the glass composition according to the method of producing a colored glass for a pharmaceutical container of the present invention is limited as described above are described in detail below. The same applies to the glass composition of the colored glass for a pharmaceutical container of the present invention, and hence the description thereof is omitted.

$Fe_2O_3$ is used as a coloring component, and has an effect of reducing a transmittance in a long-wavelength region (from 590 nm to 610 nm). The content of $Fe_2O_3$ is from 0.01% to 5%, preferably from 0.05% to 3%, from 0.1% to 2.5%, from 0.2% to 2.3%, from 0.3% to 2%, from 0.4% to 1.8%, from 0.5% to 1.5%, from 0.55% to 1.4%, or from 0.6% to 1.3%, particularly preferably from 0.6% to 1.2%. When the content of $Fe_2O_3$ is too large, in the case where the glass is turned into a pharmaceutical container, iron is liable to be mixed in a drug owing to an increase in elution amount of iron, and there is a risk in that the elution amount specified in the Japanese Pharmacopoeia is not satisfied. In addition, when the content of $Fe_2O_3$ is too small, the effect of reducing the transmittance cannot be exhibited.

$TiO_2$ is used as a coloring component, and has an effect of reducing a transmittance in a short-wavelength region (from 290 nm to 450 nm). The content of $TiO_2$ is from 0.01% to 5%, preferably from 0.05% to 4.8%, from 0.1% to 4.6%, from 0.1% to 4.5%, from 0.5% to 4.3%, from 0.7% to 4.1%, from 1% to 4%, from 1.2% to 3.9%, from 1.5% to 3.8%, from 1.6% to 3.7%, or from 1.8% to 3.6%, particularly preferably from 2.0% to 3.5%. When the content of $TiO_2$ is too large, a devitrified product of $TiO_2$ is liable to be generated, resulting in a reduction in productivity. When the content of $TiO_2$ is too small, the effect of reducing the transmittance cannot be exhibited.

$SiO_2$ is a main glass forming oxide. The content of $SiO_2$ is from 65% to 75%, preferably from 65% to 73%. When the content of $SiO_2$ is too large, the meltability of the glass is reduced. When the content of $SiO_2$ is too small, the mechanical strength of the glass is reduced, or the chemical durability of the glass is reduced and thus a glass component is liable to be mixed in a drug.

$B_2O_3$ is a component which increases the meltability of the glass. The content of $B_2O_3$ is from 0% to 20%, preferably from 0.1% to 18% or from 0.5% to 16%, more preferably from 5% to 15%, particularly preferably from 8% to 13%. When the content of $B_2O_3$ is too small, the viscosity of the glass is increased and thus the meltability and the formability of the glass are liable to be reduced. When the content of $B_2O_3$ is too large, the chemical durability is reduced. However, from the viewpoint of reducing delamination in a pharmaceutical container, the content of $B_2O_3$ may be reduced or $B_2O_3$ may be omitted.

$Al_2O_3$ is a component which suppresses the devitrification of the glass and increases the chemical durability. The content of $Al_2O_3$ is from 1% to 10%, preferably from 2% to 10%, more preferably from 3% to 9%, particularly preferably from 5% to 8%. When the content of $Al_2O_3$ is too large, the meltability of the glass is reduced and thus cords, bubbles, or the like are liable to be generated. When the content of $Al_2O_3$ is too small, the chemical durability is reduced.

$R_2O$, that is, an alkali metal oxide is a component which increases the meltability of the glass and increases a thermal expansion coefficient. The total content of $R_2O$ is from 1% to 10%, preferably from 5% to 10%, more preferably from 5% to 9%, particularly preferably from 5% to 8%. When the total content of $R_2O$ is too large, the chemical durability is reduced, and the thermal expansion coefficient is excessively increased, with the result that the glass having been processed is liable to be broken. When the total content of $R_2O$ is too small, it becomes difficult to exhibit the above-mentioned effects.

In addition, part of $Na_2O$ may be replaced by $K_2O$ or $Li_2O$. When part of $Na_2O$ is replaced by $K_2O$, the chemical durability is increased. However, when the content of $K_2O$ is more than 3.5%, the viscosity of the glass is increased and thus the meltability is reduced, and when the content of $K_2O$ is less than 0.2%, it becomes difficult to exhibit the above-mentioned effect.

R'O, that is, CaO and BaO are each a component which increases the meltability and the chemical durability of the glass. The total content of R'O is from 1% to 5%, preferably from 1% to 4%, more preferably from 1% to 3%. When the total content of R'O is too large, the thermal expansion coefficient is excessively increased, and a specific gravity is increased. When the total content of R'O is too small, it becomes difficult to exhibit the above-mentioned effects.

CaO is a component which increases the meltability and the chemical durability of the glass. The content of CaO is preferably from 0% to 3%, more preferably from 0.1% to 2%, particularly preferably from 0.1% to 1.4%. When the content of CaO is too large, the acid resistance of the glass is liable to be reduced, and besides, a crystal containing Ca is liable to be precipitated from the glass, resulting in a reduction in productivity. In addition, when the content of CaO is too small, it becomes difficult to exhibit the above-mentioned effects.

BaO is a component which reduces the viscosity of the glass and improves the devitrification resistance. The content of BaO is preferably from 0% to 4%, more preferably from 0.5% to 3%, still more preferably from 1% to 2%. When the content of BaO is too large, the strain point of the glass is reduced and thus heat resistance is liable to be reduced. Besides, a crystal containing Ba is liable to be precipitated from the glass, resulting in a reduction in productivity. In addition, when the content of BaO is too small, it becomes difficult to exhibit the above-mentioned effects.

As a fining agent, any fining agent, such as Cl, $SO_3$, or $Sb_2O_3$, may be used.

When such glass composition is adopted, it becomes easy to obtain a colored glass for a pharmaceutical container in which the transmittance of the glass satisfies the standards of the Japanese Pharmacopoeia.

In addition, while the colored glass of the present invention is suitable as a colored glass for a pharmaceutical container as described above, the colored glass of the present invention may also be used as a colored glass for a container other than for pharmaceutical applications.

A colored glass for a container of the present invention comprises as a glass composition, in terms of mass %, 65% to 75% of $SiO_2$, 0% to 20% of $B_2O_3$, 1% to 10% of $Al_2O_3$, 1% to 10% of $R_2O$, where R represents at least one or more kinds of Li, Na, and K, 1% to 5% of R'O, where R' represents at least one or more kinds of Ca and Ba, 0.01% to 5% of $Fe_2O_3$, and 0.01% to 5% of $TiO_2$ and further satisfies a relational expression of $1.00 \leq [Fe_2O_3 \text{ (content of } Fe_2O_3)] \times [TiO_2 \text{ (content of } TiO_2)] < 6.00$.

The colored glass of the present invention is excellent in light shading property, and hence a content is less liable to be altered through light irradiation, and is excellent in function of blocking ultraviolet light. Therefore, the colored glass of the present invention is particularly suitable when the content is to be protected from light degradation. For example, the colored glass of the present invention may also be suitably used for bio-related applications, experimental instruments, such as a petri dish and a beaker, cosmetic bottles, beverage bottles, food containers, and the like.

The glass composition of the colored glass for a pharmaceutical container of the present invention having been described in detail may be appropriately adopted as the glass composition of the colored glass for a container of the present invention, and the description thereof is omitted herein.

Examples

The present invention is hereinafter described in detail by way of Examples.

Glasses of the present invention (Sample Nos. 1 to 18) and Comparative Examples (Sample Nos. 19 to 22) are shown in Tables 1 to 3.

TABLE 1

| wt % | No. 1 | No. 2 | No. 3 | No. 4 | No. 5 | No. 6 | No. 7 |
|---|---|---|---|---|---|---|---|
| $SiO_2$ | 72.04 | 71.46 | 71.46 | 71.46 | 71.46 | 71.46 | 71.46 |
| $Al_2O_3$ | 5.4 | 5.4 | 5.4 | 5.4 | 5.4 | 5.4 | 5.4 |
| $B_2O_3$ | 9.5 | 9.5 | 9.5 | 9.5 | 9.5 | 9.5 | 9.5 |
| CaO | 0.8 | 0.8 | 0.8 | 0.8 | 0.8 | 0.8 | 0.8 |
| BaO | 1.3 | 1.3 | 1.3 | 1.3 | 1.3 | 1.3 | 1.3 |
| $Na_2O$ | 5.75 | 5.75 | 5.75 | 5.75 | 5.75 | 5.75 | 5.75 |
| $K_2O$ | 2.35 | 2.35 | 2.35 | 2.35 | 2.35 | 2.35 | 2.35 |
| Cl | 0.08 | 0.08 | 0.08 | 0.08 | 0.08 | 0.08 | 0.08 |
| $Fe_2O_3$ | 0.57 | 0.76 | 0.76 | 0.76 | 0.76 | 0.76 | 0.76 |
| $TiO_2$ | 2.21 | 2.6 | 2.6 | 2.6 | 2.6 | 2.6 | 2.6 |
| $Fe_2O_3 \times TiO_2$ | 1.26 | 1.98 | 1.98 | 1.98 | 1.98 | 1.98 | 1.98 |
| $Fe_2O_3/TiO_2$ | 0.26 | 0.29 | 0.29 | 0.29 | 0.29 | 0.29 | 0.29 |
| Metal Al | 0.06 | 0.03 | 0.06 | 0.09 | 0.06 | 0.06 | 0.09 |
| Metal S | — | — | — | — | 0.01 | — | — |
| Transmittance [%] at 450 nm | 44.7 | 45.1 | 32.2 | 24.5 | 25.6 | 41.8 | 34.5 |
| Transmittance [%] at 590 nm | 75.9 | 75.3 | 70.2 | 66.0 | 66.2 | 73.9 | 71.0 |
| Fe raw material | Triiron tetraoxide | Triiron tetraoxide | Triiron tetraoxide | Triiron tetraoxide | Triiron tetraoxide | Ferric oxide | Ferric oxide |
| Thickness [mm] | 1.0 | 1.0 | 1.0 | 1.0 | 1.0 | 1.0 | 1.0 |

TABLE 2

| wt % | No. 8 | No. 9 | No. 10 | No. 11 | No. 12 | No. 13 | No. 14 | No. 15 |
|---|---|---|---|---|---|---|---|---|
| $SiO_2$ | 71.26 | 71.27 | 71.27 | 70.88 | 72.04 | 71.65 | 71.65 | 71.66 |
| $Al_2O_3$ | 5.4 | 5.4 | 5.4 | 5.4 | 5.4 | 5.4 | 5.4 | 5.4 |
| $B_2O_3$ | 9.5 | 9.5 | 9.5 | 9.5 | 9.5 | 9.5 | 9.5 | 9.5 |
| CaO | 0.8 | 0.8 | 0.8 | 0.8 | 0.8 | 0.8 | 0.8 | 0.8 |
| BaO | 1.3 | 1.3 | 1.3 | 1.3 | 1.3 | 1.3 | 1.3 | 1.3 |
| $Na_2O$ | 5.75 | 5.75 | 5.75 | 5.75 | 5.75 | 5.75 | 5.75 | 5.75 |
| $K_2O$ | 2.35 | 2.35 | 2.35 | 2.35 | 2.35 | 2.35 | 2.35 | 2.35 |
| Cl | 0.08 | 0.08 | 0.08 | 0.08 | 0.08 | 0.08 | 0.08 | 0.08 |
| $Fe_2O_3$ | 0.76 | 0.95 | 0.95 | 0.95 | 0.57 | 0.57 | 0.76 | 0.95 |
| $TiO_2$ | 2.8 | 2.6 | 2.6 | 2.99 | 2.21 | 2.6 | 2.41 | 2.21 |
| $Fe_2O_3 \times TiO_2$ | 2.13 | 2.47 | 2.47 | 2.84 | 1.26 | 1.48 | 1.83 | 2.10 |
| $Fe_2O_3/TiO_2$ | 0.27 | 0.37 | 0.37 | 0.32 | 0.26 | 0.22 | 0.32 | 0.43 |
| Metal Al | 0.09 | 0.06 | 0.09 | 0.09 | 0.06 | 0.09 | 0.09 | 0.06 |
| Metal S | — | — | — | — | — | — | — | — |
| Transmittance [%] at 450 nm | 48.5 | 48.5 | 45.9 | 38.5 | 18.8 | 8.9 | 7.1 | 7.9 |
| Transmittance [%] at 590 nm | 78.2 | 77.3 | 76.4 | 73.4 | 59.4 | 53.2 | 47.7 | 45.8 |
| Fe raw material | Triiron tetraoxide | Triiron tetraoxide | Triiron tetraoxide | Triiron tetraoxide | Triiron tetraoxide | Triiron tetraoxide | Triiron tetraoxide | Triiron tetraoxide |
| Thickness [mm] | 0.45 | 0.45 | 0.45 | 0.45 | 2.2 | 2.2 | 2.2 | 2.2 |

TABLE 3

| wt % | No. 16 | No. 17 | No. 18 | No. 19 | No. 20 | No. 21 | No. 22 |
|---|---|---|---|---|---|---|---|
| $SiO_2$ | 71.66 | 70.7 | 69.52 | 73.12 | 69.32 | 73.12 | 69.32 |
| $Al_2O_3$ | 5.4 | 5.8 | 5.8 | 5.4 | 5.4 | 5.4 | 5.4 |
| $B_2O_3$ | 9.5 | 7.5 | 11 | 9.5 | 9.5 | 9.5 | 9.5 |
| CaO | 0.8 | 0.5 | 0.6 | 0.8 | 0.8 | 0.8 | 0.8 |
| BaO | 1.3 | 2.1 | 1.3 | 1.3 | 1.3 | 1.3 | 1.3 |
| $Na_2O$ | 5.75 | 6.1 | 5.9 | 5.75 | 5.75 | 5.75 | 5.75 |
| $K_2O$ | 2.35 | 1.5 | 1.2 | 2.35 | 2.35 | 2.35 | 2.35 |
| Cl | 0.08 | — | 0.08 | 0.08 | 0.08 | 0.08 | 0.08 |
| $Fe_2O_3$ | 1.2 | 1.2 | 1.4 | 0.3 | 1.5 | 0.3 | 1.5 |
| $TiO_2$ | 4.5 | 4.5 | 3.2 | 1.4 | 4.0 | 1.4 | 4.0 |
| $Fe_2O_3 \times TiO_2$ | 5.40 | 5.40 | 4.48 | 0.42 | 6.00 | 0.42 | 6.00 |
| $Fe_2O_3/TiO_2$ | 0.27 | 0.27 | 0.26 | 0.21 | 0.38 | 0.21 | 0.38 |

TABLE 3-continued

| wt % | No. 16 | No. 17 | No. 18 | No. 19 | No. 20 | No. 21 | No. 22 |
|---|---|---|---|---|---|---|---|
| Metal Al | 0.03 | 0.03 | 0.04 | 0.09 | 0.09 | 0.06 | 0.06 |
| Metal S | — | — | — | — | — | — | — |
| Transmittance [%] at 450 nm | 8.8 | 5.2 | 6.9 | 64.5 | 3.7 | 66 | 5.6 |
| Transmittance [%] at 590 nm | 46.2 | 45.2 | 47.1 | 83.1 | 35.1 | 84.5 | 41.2 |
| Fe raw material | Triiron tetraoxide | Triiron tetraoxide | Triiron tetraoxide | Triiron tetraoxide | Triiron tetraoxide | Triiron tetraoxide | Triiron tetraoxide |
| Thickness [mm] | 2.2 | 2.2 | 2.2 | 1.0 | 1.0 | 1.0 | 1.0 |

First, raw materials were blended so as to give a composition shown in the tables to produce a glass batch. In order to adjust the redox state of a glass, iron raw materials having various redox states, such as ferric oxide and triiron tetraoxide, were each used as an iron raw material, and metal aluminum and/or metal sulfur was used as a reducing agent.

Next, the glass raw materials (500 g of glass) were loaded into a platinum crucible, and melted at 1,600° C. for 4 hours and formed through rapid cooling. After that, the resultant glass was processed into a thickness shown in the tables, and the glass surfaces were each mirror finished.

The transmittance of the glass having been processed was measured with a spectrophotometer (SHIMADZU UV-3100). A measurement wavelength region was set to from 300 nm to 800 nm, a slit width was set to 5 nm, a scanning speed was set to a medium speed, and a sampling pitch was set to 1 nm.

In each of Sample Nos. 1 to 18, a value for [$Fe_2O_3$ (content of $Fe_2O_3$)]×[$TiO_2$ (content of $TiO_2$)] satisfied the range of from 1.00 to less than 6.00, and hence, at the respective thicknesses, while the productivity was maintained, the transmittance of the glass was able to be controlled so as to satisfy the standards of a transmittance specified in the Japanese Pharmacopoeia by adding the reducing agent.

In particular, in each of Sample Nos. 1 to 7, the transmittance of the glass in which the thickness of the formed glass was 1 mm satisfied the transmittance specified in the Japanese Pharmacopoeia irrespective of the kind and the content of the reducing agent.

In addition, in each of Sample Nos. 8 to 11, a value for [$Fe_2O_3$ (content of $Fe_2O_3$)]×[$TiO_2$ (content of $TiO_2$)] was 1.20 or more, and hence the transmittance of the glass in which the thickness of the formed glass was less than 1 mm satisfied the transmittance specified in the Japanese Pharmacopoeia.

In addition, in each of Sample Nos. 12 to 18, a value for ($Fe_2O_3$ (content of $Fe_2O_3$)×[$TiO_2$ (content of $TiO_2$)] was 5.40 or less, and hence the transmittance of the glass in which the thickness of the formed glass was 1 mm or more satisfied the transmittance specified in the Japanese Pharmacopoeia.

Meanwhile, in each of Sample Nos. 19 to 22 serving as Comparative Examples, a value for [$Fe_2O_3$ (content of $Fe_2O_3$)]×$TiO_2$ (content of $TiO_2$) was outside the range of the present invention, and hence the transmittance of the obtained glass was significantly apart from a value for the transmittance specified in the Japanese Pharmacopoeia. Therefore, the transmittance of the glass was not able to satisfy the standards of the Japanese Pharmacopoeia merely by changing the content of the reducing agent so that the productivity was able to be maintained. It is considered that the content of the reducing agent is required to be significantly changed, or the production conditions, such as a melting temperature, are required to be changed, in order to allow the transmittance of the glass to satisfy the standards of the Japanese Pharmacopoeia, and hence a reduction in productivity and deterioration in glass quality occur.

The invention claimed is:

1. A colored glass for a pharmaceutical container, comprising as a glass composition, in terms of mass %, 65% to 75% of $SiO_2$, 0% to 20% of $B_2O_3$, 1% to 10% of $Al_2O_3$, 1% to 10% of $R_2O$, where R is selected from at least one of Li, Na, and K, 1% to 5% of R'O, where R' is selected from at least one of Ca and Ba, 0.01% to 5% of $Fe_2O_3$, and 0.01% to 5% of $TiO_2$, further satisfying a relational expression of $1.00 \leq [Fe_2O_3$ (content of $Fe_2O_3$)]×[$TiO_2$ (content of $TiO_2$)] $\leq 3.50$, and satisfying a transmittance (ultraviolet transmittance) specified in "Light transmission test for light-resistant containers" of the Japanese Pharmacopoeia, section 7.01.

2. The colored glass for a pharmaceutical container according to claim 1, wherein the colored glass has a thickness of less than 1 mm and satisfies a relational expression of $1.20 \leq [Fe_2O_3$ (content of $Fe_2O_3$)]×[$TiO_2$ (content of $TiO_2$)] in terms of mass %.

* * * * *